United States Patent
Gaiser et al.

(10) Patent No.: US 8,423,321 B2
(45) Date of Patent: Apr. 16, 2013

(54) TRANSFER OF A COMPONENT WITH EFFECT ON THE SAFETY FUNCTION FROM THE SAFETY-RELEVANT AREA

(75) Inventors: Martin Gaiser, Alpirsbach (DE);
Juergen Haas, Oberwolfach (DE);
Juergen Lienhard, Fischerbach (DE);
Juergen Motzer, Gengenbach (DE)

(73) Assignee: Vega Grieshaber KG, Wolfach (DE)

( * ) Notice: Subject to any disclaimer, the term of this patent is extended or adjusted under 35 U.S.C. 154(b) by 246 days.

(21) Appl. No.: 12/603,918

(22) Filed: Oct. 22, 2009

(65) Prior Publication Data
US 2010/0114530 A1 May 6, 2010

Related U.S. Application Data

(60) Provisional application No. 61/111,097, filed on Nov. 4, 2008.

(30) Foreign Application Priority Data

Nov. 4, 2008 (EP) ..................................... 08168296

(51) Int. Cl.
*G01R 31/00* (2006.01)
*G06F 11/30* (2006.01)
*G06F 19/00* (2011.01)

(52) U.S. Cl.
USPC ..... 702/182; 73/865.9; 324/537; 324/762.06; 324/763.01; 361/1; 702/183; 714/1; 714/25; 714/47.1; 716/136

(58) Field of Classification Search .................. 702/116, 702/117, 183, 1, 108, 127, 182, 187, 189; 714/183, 1, 25, 47.1, 100, 699, 724, E11.001, 714/E11.002, E11.02, E11.179; 73/865.8, 73/865.9; 324/500, 537, 762.01, 762.06, 324/763.01; 340/500, 540, 635, 653, 679; 361/1; 703/1; 716/100, 136; *G01R 31/00; G06F 11/00, 11/30, 11/32, 17/00, 17/40, G06F 19/00*

See application file for complete search history.

(56) References Cited

U.S. PATENT DOCUMENTS

| 2,883,255 | A | * | 4/1959 | Anderson | 346/34 |
| 3,309,542 | A | * | 3/1967 | Elliot | 361/1 |
| 3,321,613 | A | * | 5/1967 | Searle | 702/182 |
| 3,445,679 | A | * | 5/1969 | Meyer et al. | 361/1 |
| 3,611,053 | A | * | 10/1971 | Rowell | 361/160 |
| 3,696,364 | A | * | 10/1972 | Lavelle | 340/531 |
| 4,006,448 | A | * | 2/1977 | Arai et al. | 340/459 |

(Continued)

FOREIGN PATENT DOCUMENTS

| EP | 0610711 A1 | * | 8/1994 |
| EP | 2182331 A1 | * | 5/2010 |

(Continued)

*Primary Examiner* — Edward Cosimano
(74) *Attorney, Agent, or Firm* — Fay Kaplun & Marcin, LLP

(57) ABSTRACT

An electronic module for level measurements, pressure measurements or density measurements is disclosed. In the module, a safety-relevant function is transferred into an area that is categorized as safety-uncritical. In order to prevent malfunctions, a diagnostic function is performed in the safety-critical area of the electronic module in order to check the transferred function. This diagnostic function is also checked with respect to its effectiveness during the safety-oriented operation. Suitable measures can be initiated in case an error is detected.

20 Claims, 3 Drawing Sheets

U.S. PATENT DOCUMENTS

| | | | | |
|---|---|---|---|---|
| 4,331,953 A | * | 5/1982 | Blevins et al. | 340/539.26 |
| 4,443,710 A | * | 4/1984 | Hofmann et al. | 307/80 |
| 4,906,977 A | | 3/1990 | Huey-Jeng | 340/626 |
| 5,966,305 A | * | 10/1999 | Watari et al. | 700/82 |
| 6,711,729 B1 | * | 3/2004 | McElvain et al. | 716/105 |
| 7,139,676 B2 | * | 11/2006 | Barford | 702/183 |
| 7,370,211 B2 | * | 5/2008 | Rindborg et al. | 713/191 |
| 7,380,276 B2 | * | 5/2008 | Saha et al. | 726/22 |
| 2003/0188221 A1 | * | 10/2003 | Rasmussen et al. | 714/11 |
| 2004/0243810 A1 | * | 12/2004 | Rindborg et al. | 713/176 |
| 2005/0273605 A1 | * | 12/2005 | Saha et al. | 713/166 |
| 2007/0273508 A1 | * | 11/2007 | Lalla et al. | 340/540 |

FOREIGN PATENT DOCUMENTS

| | | |
|---|---|---|
| GB | 2 251 506 | 7/1992 |
| WO | 00/03209 | 1/2000 |
| WO | 2004/104525 | 12/2004 |
| WO | WO2005/064424 * | 7/2005 |

* cited by examiner

TRANSFER OF A COMPONENT WITH EFFECT ON THE SAFETY FUNCTION FROM THE SAFETY-RELEVANT AREA

REFERENCE TO RELATED APPLICATIONS

This application claims the benefit of the filing date of EP Patent Application Serial No. 08 168 296.5 filed Nov. 4, 2008 and expired U.S. Provisional Patent Application Ser. No. 61/111,097 filed Nov. 4, 2008, the disclosure of which applications is hereby incorporated herein by reference.

FIELD OF THE INVENTION

The present invention pertains to level, pressure and density measurements. The invention specifically pertains to an electronic module for level measurements, pressure measurements or density measurements, a method for measuring and determining a level, a pressure or a density of a medium in a container, a field device, a control device and a display and operating unit.

TECHNOLOGICAL BACKGROUND

The safety requirement level to be fulfilled determines whether a function of a technical device is categorized as safety-critical or safety-uncritical. The safety requirement level is a term from the field of functional safety and also referred to as safety integration level (SIL). The desired safety requirement level defines the safety-oriented construction principle of the device that needs to be observed so that the risk of a malfunction fulfills the specified requirements.

If a function is categorized as safety-critical, this means, for example, that this function needs to fulfill the requirements of SIL3 or even SIL4. If a function is categorized as safety-uncritical, this means, for example, that it does not have to fulfill a SIL requirement.

In many cases, technical devices in the field of level measurements, pressure measurements or density measurements that fulfill a safety function (e.g., in the sense of SIL) internally consist of two areas. One area is the safety-critical or safety-relevant area that is responsible for the safety function. The other area is a safety-uncritical area that does not influence the safety function.

Depending on the safety level, all hardware and software components that belong to the safety-relevant area of a device not only require much time and effort during the development phase of the device, but also over the entire life cycle thereof. In contrast, software and/or hardware components in the area that is safety-irrelevant usually can be developed and serviced in a much simpler and more cost-efficient fashion.

Components that have a direct influence on the safety function are usually assigned to the safety-relevant area during the planning phase of the device such that these components can be developed in accordance with the safety function requirements. However, this is not absolutely imperative in all instances and can result in unnecessarily high expenditures and costs.

SUMMARY OF THE INVENTION

The present invention proposes an electronic module for filling level measurements, e.g. of a medium inside a container pressure measurements or density measurements, a field device with an electronic module, a control device with an electronic module, a display and operating unit with an electronic module, as well as a method for measuring and determining a filling level, a pressure or a density of a medium in a container.

The described embodiments likewise pertain to the electronic module, the field device, the control device, the display and operating unit and the method. In other words, the characteristics described below with reference to the electronic module can also be implemented in the field device, the control device, the display and operating unit or the method and vise versa.

According to one embodiment of the invention, an electronic module for filling level measurements, pressure measurements and/or density measurements is disclosed, wherein said electronic module features a first area and a second area. The first area is categorized as a safety-critical and the second area is categorized as safety-uncritical. The electronic module is designed for performing a safety function, wherein the second area is designed, among other things, for performing a transferred function (i.e. a function which is outsourced from the first area into the second area) of the electronic module that is categorized as a safety-critical and affects the safety function.

In other words, a component or a function that normally needs to be assigned to the safety-relevant area is transferred from this safety-critical area into a safety-uncritical area. This may make it possible to lower the expenditures with respect to the development and the integration of this component.

This may make available an improved electronic module for level measurements, pressure measurements and/or density measurements.

According to another embodiment of the invention, the first area that is categorized as safety-critical is designed, among other things, for performing a diagnostic function that makes it possible to check whether the transferred function is performed in the second area.

Consequently, a component that functionally affects the safety function is transferred into the safety-irrelevant area. This may mean that this component no longer has to fulfill the high quality requirements of the safety function. Due to the implementation of the diagnostic measure (diagnostic function) in the safety-relevant area, however, it may be ensured that all errors of the now transferred components are detected, particularly if they have a negative affect on the safety function.

According to another embodiment of the invention, the diagnostic function is designed for detecting all known errors of the transferred function, i.e. all errors which are known that they may occur at some time.

According to another embodiment of the invention, the first area that is categorized as safety-critical is furthermore designed for taking suitable measures, wherein these measures are taken if the aforementioned diagnostic function discovers an error in the transferred function. For example, the diagnostic component may not perform any actions that go beyond the diagnostic scope. These actions are still reserved for other components that need to be arranged in the first area.

The defect may be repaired and, if applicable, the source of the defect may also be eliminated by taking a suitable measure. If neither is possible, the system transfers into a predefined safe state. This state is maintained as long as a malfunction of the transferred function is diagnosed.

Consequently, the effectiveness of the diagnosis may be periodically verified during the safety-critical operation of the electronic module. For example, a certain malfunction may be briefly simulated in order to check the effectiveness of the diagnostic measure.

It may therefore be precluded that a defect in a transferred function (component) lowers the quality of the safety function.

According to another embodiment of the invention, the transferred function is designed for continuously controlling an internal variable of the electronic module. This may concern, for example, the control of a certain frequency of a level sensor. The accuracy of this frequency may influence the accuracy of the measurement. In this case, the control may comprise a control program, as well as a circuit, for example, in the form of a microcontroller.

According to another embodiment of the invention, the transferred function is designed for adjusting a current output of a 4 . . . 20 mA two-wire loop. In this case, the adjusted current output corresponds to the measured value and serves for the transmission of the measured value.

According to another embodiment of the invention, the transferred function concerns the determination of measured values on the basis of sensor measuring data, the deduction of other measured values on the basis of already determined measured values or the output of measured values.

It is also possible to transfer several functions from the safety-relevant area into the safety-irrelevant area.

According to another embodiment of the invention, the electronic module is integrated into a level measuring device, a pressure measuring device or a density measuring device.

According to another embodiment of the invention, the electronic module is integrated into a control device for the level measuring device, the pressure measuring device or the density measuring device.

According to another embodiment of the invention, the electronic module is integrated into a display and operating unit for the level measuring device, the pressure measuring device or the density measuring device.

According to another embodiment of the invention, a field device with an above-described electronic module is disclosed.

According to another embodiment of the invention, a control device with an above-described electronic module is disclosed.

According to another embodiment of the invention, a display and operating unit with an above-described electronic module is disclosed.

According to another embodiment of the invention, a method for measuring and determining a level or a pressure or a density of a medium in a container by means of a field device is disclosed, wherein a safety function is performed in a first area of the electronic module that is categorized as safety-critical. In addition, a transferred function of the electronic module is performed in a second area of the electronic module that is categorized as safety-uncritical. This transferred function concerns a function that is categorized as safety-critical and affects the safety function of the field device.

According to another embodiment of the invention, the method furthermore comprises the following steps: performing a diagnostic function in the first area in order to check if the transferred function is performed in the second area; taking a suitable measure if an error in the transferred function is detected; periodically checking the effectiveness of the diagnostic function.

The effectiveness of the diagnostic function naturally may also be checked within irregular intervals, for example, in dependence on the frequency, with which the individual level, pressure or density measurements are carried out. Since the diagnostic measure fulfills a safety-critical function, it should forward a discovered error to a higher instance. This higher instance (usually a special component in the first or safety-critical area) then takes a suitable measure.

One advantage of the invention may be seen in that the realization of the diagnostic measures in the safety-relevant area, as well as the implementation of the components outside the safety-relevant area, may be easier and more cost-efficient than a complete implementation of the corresponding component in the safety-relevant area.

Due to the transfer of complex functions that directly contribute to the safety function out of the safety-relevant area into the safety-uncritical area, the quality of the safety function may not be lowered because the transferred functions are checked by means of the diagnostic function.

Embodiments of the invention are described below with reference to the figures.

DETAILED DESCRIPTION OF EMBODIMENTS

The figures show schematic illustrations that are not true-to-scale.

In the following description of the figures, identical or similar elements are identified by the same reference symbols.

Figure 1:
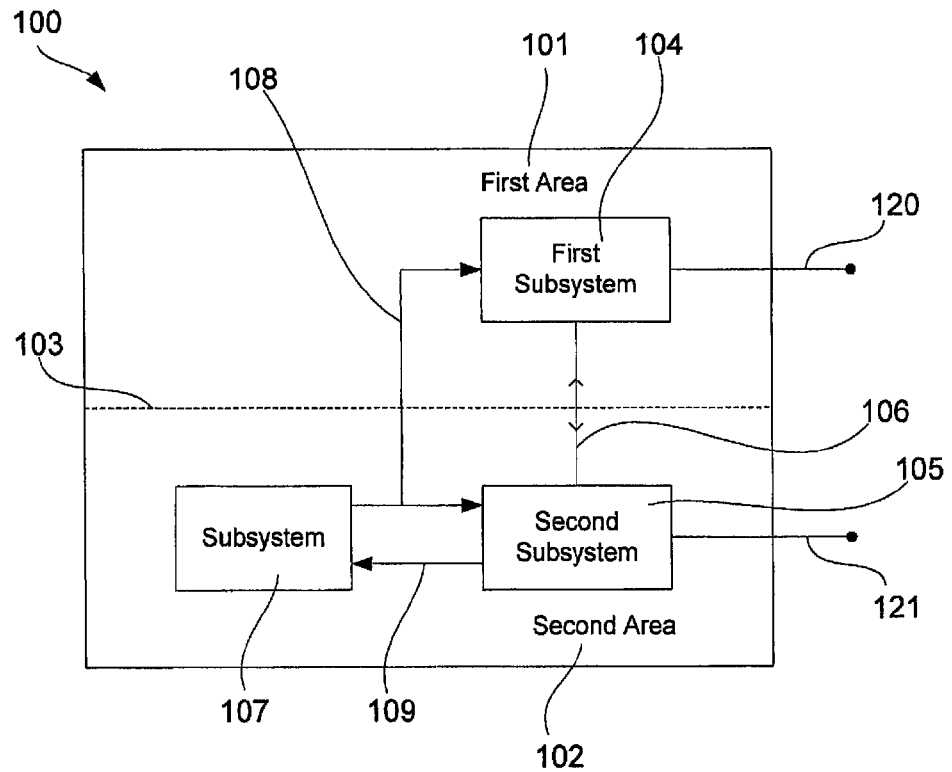
FIG. 1 shows an illustration of an electronic module according to an exemplary embodiment of the present invention.

FIG. 1 shows an electronic module 100 with a first area 101 and a second area 102. The first area 101 is categorized as safety-critical and separated from the second area 102 that is categorized as safety-uncritical (as symbolized by the broken line 103).

For example, the safety-critical area contains a first subsystem 104 in the form of, for example, a first processor and the second area 102 contains a second subsystem 105, for example, in the form of a second processor.

The two areas may also contain different data memories and circuits, etc.

In addition, a communication line 106 is provided that enables the two subsystems 104,105 to communicate with one another. In this case, the data exchange also may, for example, only be realized unidirectionally, namely from the safety-critical area 101 into the safety-uncritical area 102.

It should be noted that the two areas 101, 102 may be realized in the form of a module 100, as well as in the form of two partial modules that are separated from one another (not shown in FIG. 1).

Each of the two areas 101, 102 furthermore features an interface 120 and 121 for being connected to the outside world.

The electronic module 100 therefore has two areas, namely the safety-relevant area 101 that is responsible for the safety function and the safety-irrelevant area 102 that does not influence the safety function. One possible function that influences the safety function could consist of an internal variable being generated in the subsystem 107 in the safety-irrelevant area 102 of the electronic module and this internal variable being constantly maintained at a predetermined value by the subsystem 105 via the connection 109 (correcting variables). If an electronic module is used in a level sensor, this may concern, for example, a certain frequency of a signal. This may require a continuous control.

The controlled variable is transmitted to the subsystem 104 in the safety-critical area and likewise to the subsystem 105 in the safety-irrelevant area via the connection 108.

However, the safety function may only require this internal variable periodically and for a brief period of time in each case.

A diagnostic measure in the safety-relevant area now checks if the controlled internal variable lies in a tolerable range of values while it is needed for realizing the safety function.

In addition, the diagnostic measure is periodically checked during the safety-oriented operation of the device so as to ensure the effectiveness of the diagnostic measure. For this purpose, the internal variable may be intentionally falsified and it is then checked whether the diagnostic measure correctly reacts to this simulated error. For example, this online check of the diagnostic measure is always carried out when the safety function does not require the internal variable to be controlled. This check may also be carried out only once within the diagnostic period of the device.

This means that the control itself is transferred into the safety-irrelevant area such that the expenditures for the control may be reduced and additional degrees of freedom may be provided in comparison with a realization of the control in the safety-relevant area.

For example, if a complex signal needs to be generated in order to carry out a measurement and a simple check as to the correct generation of the signal needs to be carried out by means of a diagnostic measure, it is possible to utilize the same method as in the frequency control as long as all possible errors in generating the complex signal can be discovered and managed by means of a diagnostic measure. If this is the case, all components required for generating the aforementioned signal can be transferred into the safety-uncritical area. However, a corresponding diagnostic measure, as well as the functional check thereof, needs to be implemented in this case in the safety-critical area at the time of operation.

The functional check of the diagnostic measure at the time of operation may also be eliminated if the diagnostic measure is not realized in the form of a classic diagnostic measure, i.e., with reduced criticality. Since stricter requirements with respect to the realization of the diagnostic measure apply in this case, the risk of a failure of the diagnostic measure is minimized to such a degree that the functional check of the diagnostic measure at the time of operation is not absolutely imperative.

The described method may be implemented in a field device, as well as in a control device for a field device or an evaluation and operating unit.

Figure 2:
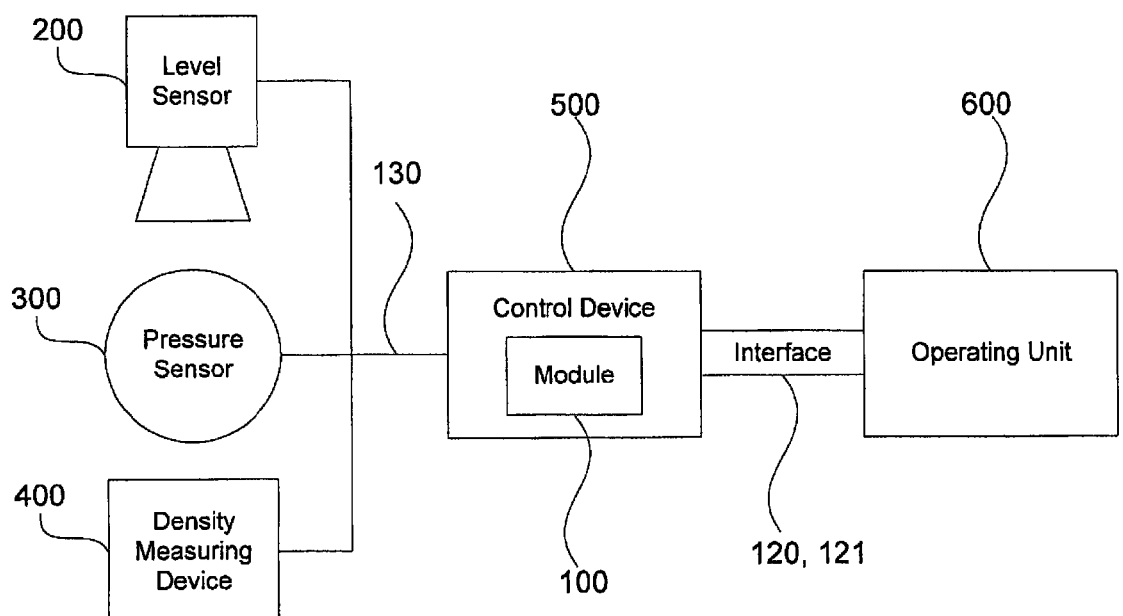
FIG. 2 shows an illustration of a measuring system according to an exemplary embodiment of the present invention.

FIG. 2 shows a measuring system according to one embodiment of the invention that can be used for level measurements, as well as for pressure and density measurements. The measuring system features one or more level sensors 200, one or more pressure sensors 300 and/or one or more density measuring devices 400. All sensors are connected to the control device 500 via a measuring bus 130. The control device 500, in turn, is connected to an evaluation and operating unit 600 via the line 120 and/or 121.

In the embodiment according to FIG. 2, the electronic module is integrated into the control device 500.

Figure 3:
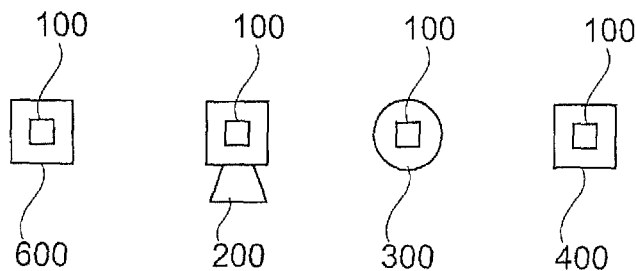
FIG. 3 shows a display and operating unit, a level measuring device, a density measuring device and a pressure measuring device according to an exemplary embodiment of the present invention.

FIG. 3 shows an embodiment of measuring sensors and an evaluation and operating unit 600, into which an electronic module 100 is respectively integrated. The measuring sensors consist of a level measuring device 200, a pressure measuring device 300 and a density measuring device 400.

In this case, the integrated electronic modules 100 may be individually adapted to the different devices, i.e., they may differ from one another. It is also possible to integrate the same universally designed electronic module 100 into all devices.

Figure 4:
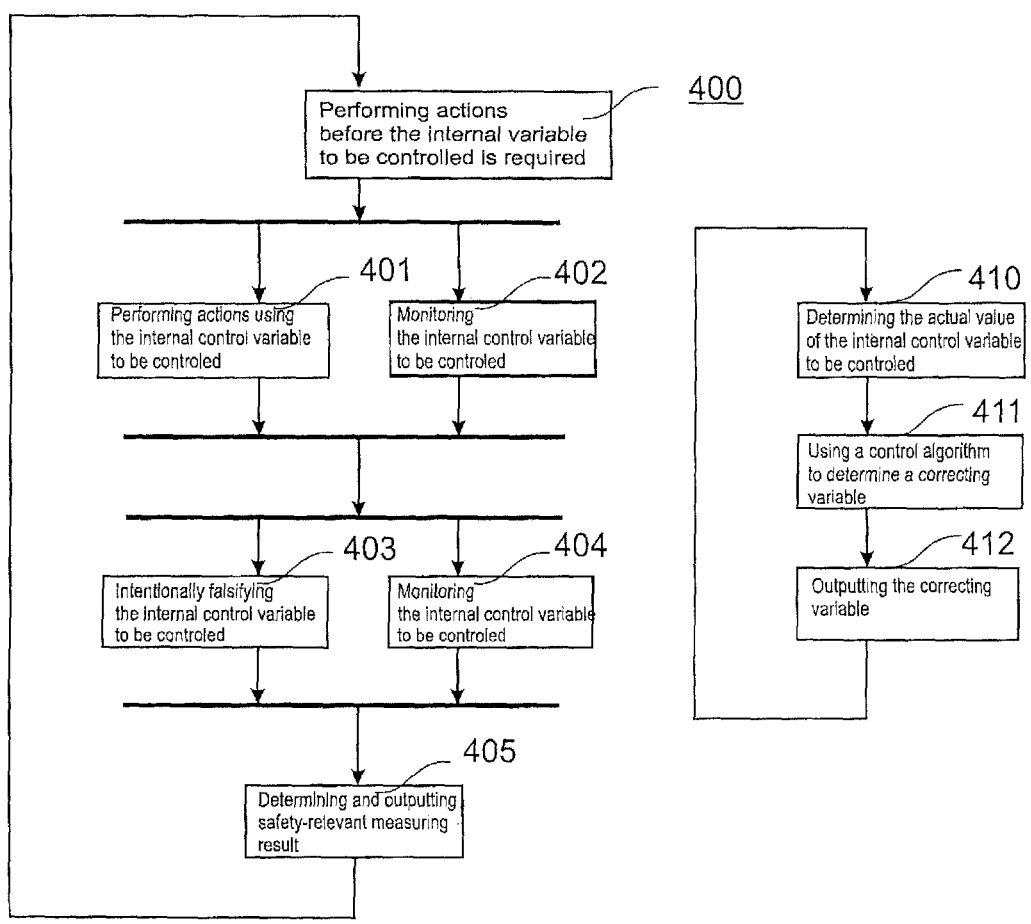
FIG. 4 shows a flow chart of a method according to an exemplary embodiment of the present invention.

FIG. 4 shows a flow chart of a method according to one embodiment of the invention. Steps 400 to 405 symbolize actions that need to be performed in order to realize the safety function. These actions are performed in the safety-critical area.

In steps 410 to 412, all actions for controlling the internal variable are performed. These actions are performed in the safety-uncritical area. In step 410, the actual value of the variable to be controlled is determined, wherein the correcting variable is determined with a control algorithm in step 411 and the correcting variable is ultimately output in step 412.

The two loops (steps 400 to 405 and steps 410 to 412) are continuously carried out in a parallel fashion and not synchronized.

In step 400, actions are performed before the internal variable to be controlled is required.

In step 401, actions are performed, in which the internal variable to be controlled is utilized. Step 402 is carried out simultaneously with step 401. In step 402, actions are performed, in which the internal variable to controlled is monitored, wherein this serves for determining whether the internal variable lies within a defined range of values that needs to be observed in order to realize the safety function.

Step 403 is also carried out simultaneously with step 404. In step 404, exactly the same actions as in step 402 are performed (monitoring of the internal variable to be controlled). In contrast to step 401, however, the internal variable to be controlled is not used in step 403, but rather intentionally falsified. This must be detected and signaled by the monitoring arrangement in step 404. Consequently, step 403 performs an online check of the monitoring arrangement that is likewise performed in steps 402 and 404.

The internal variable to be controlled also is no longer required in step 405. The safety-relevant measuring result is determined and output in this step. However, if it was determined in step 402 that the internal variable to be controlled did not lie within the required range of values during step 401 or that the online check of the monitoring arrangement failed, a new measuring result is not determined in step 405, but a suitable measure for this type of error is taken instead.

Steps 403 and 404 may not have to be performed during each measuring cycle. It may suffice if these steps are carried out once during the diagnostic period of the system.

Figure 5:
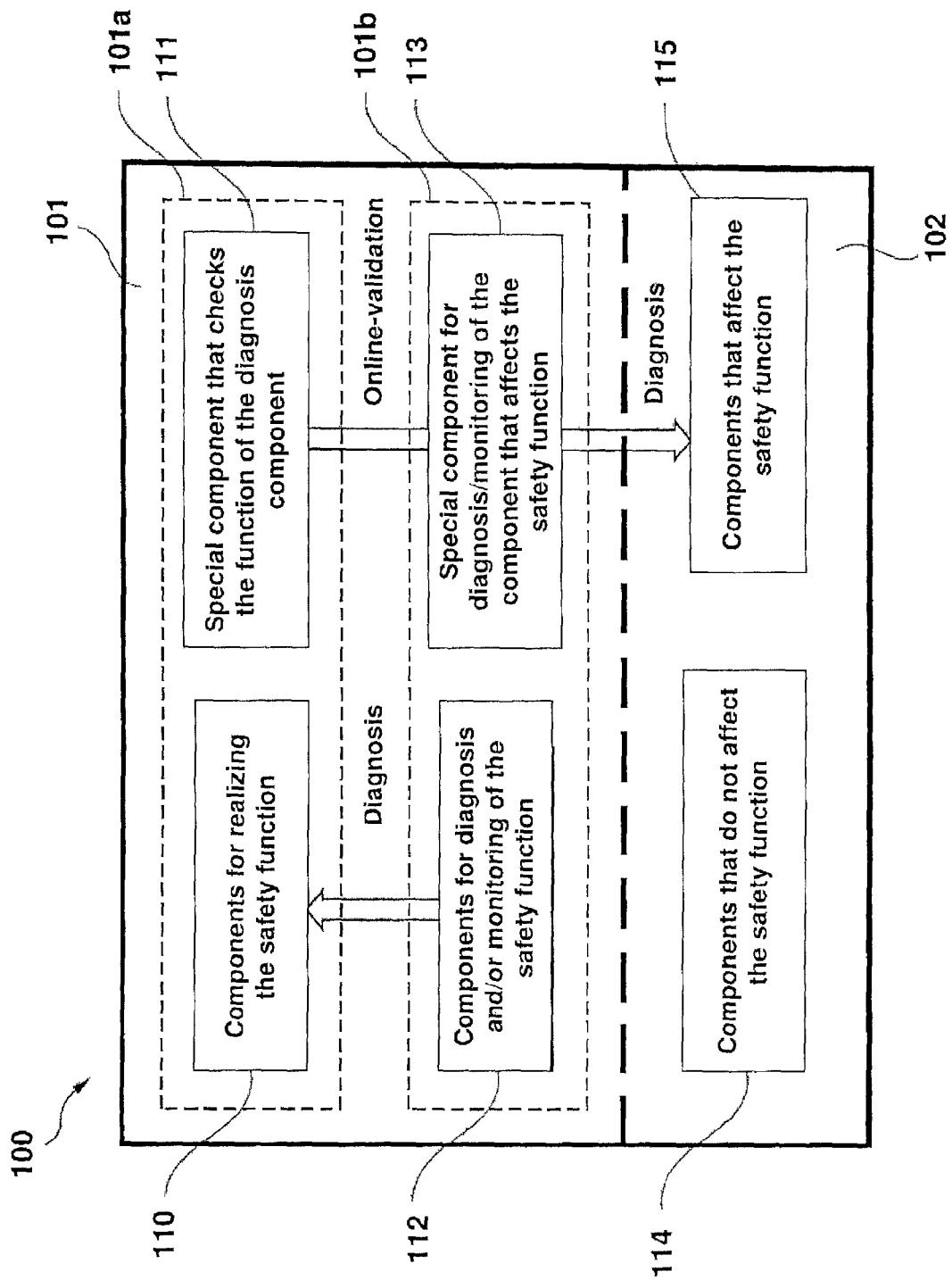
FIG. 5 shows an illustration of an electronic module according to another exemplary embodiment of the present invention.

FIG. 5 shows an illustration of an electronic module 100 according to another embodiment of the invention. The electronic module 100 has a first area 101 and a second area 102.

The area 101 is safety-critical and the area 102 is safety-uncritical. In order to clarify this, the area 101 is subdivided into the areas 101*a* and 101*b*. The area 101*a* has the highest criticality of the system and therefore requires the highest development expenditures. The area 101*b* has a lower criticality than the area 101*a* and therefore requires somewhat lower development expenditures. The area 102 has no criticality and therefore requires much lower development expenditures than the areas 101*a* and 101*b*.

The component 115 in the safety-uncritical area 102 affects the safety function of the electronic unit 100 and is transferred out of the area 101 with a high safety level into the area 102. Two measures are taken in order to prevent that this negatively influences the safety function:

Firstly, the electronic unit features a special component 113 that monitors the transferred component 115. At this point, it should be noted that the designation "component" may concern a computer program and/or hardware in the context of the invention.

The component 113 therefore is safety-relevant and initially needs to be assigned to the area 101. In more specific terms, 113 is a classic diagnostic component and therefore can be assigned to the area 101b of reduced criticality.

Secondly, the electronic unit also features a component 111 that checks the function of the component 113 during the safety-oriented operation. Consequently, this concerns a diagnosis of the diagnosis or, in other words, an online check of the diagnostic component 113 or the diagnostic measure, respectively. In order to ensure that this online check has an effect on the safety engineering, the corresponding component 111 is arranged in the region of high criticality 101a.

The expenditures for realizing the component 115 can be significantly lowered in this fashion. However, additional components 111 and 113 need to be realized. If the reduction of the expenditures for realizing the component 115 results in savings that exceed the additional expenditures for realizing the components 111 and 113, the electronic unit 100 can be realized in a more cost-efficient fashion.

The safety-uncritical area 102 furthermore contains components that do not affect the safety function 114. The area of reduced criticality 101b contains components for diagnostics and/or monitoring 112. The area with a high safety level 101a contains components for realizing the safety function 110 that are monitored by the components 112 in the form of a diagnostic function.

As a supplement, it should be noted that "comprising" and "featuring" do not exclude other elements or steps, and that "an" or "a" does not exclude a plurality. It should furthermore be noted that characteristics or steps that were described with reference to one of the above embodiments can also be used in combination with other characteristics or steps of other above-described embodiments. The reference symbols in the claims should not be interpreted in a restrictive sense.

What is claimed is:

1. An electronic module for one of a level measurement, a pressure measurement and a density measurement, comprising:
    a first area being categorized as safety-critical; and
    a second area being categorized as safety-uncritical, the second area performing a transferred function of the module and the first area not performing the transferred function,
    wherein the module performs a safety function, the transferred function being categorized as a safety-critical and affects the safety function; and
    wherein the first area performs a diagnostic function in order to check an execution of the transferred function in the second area.

2. The electronic module of claim 1, wherein the diagnostic function detects an error in the transferred function.

3. The electronic module of claim 1, wherein the module takes a suitable measure if an error is detected in the transferred function.

4. The electronic module of claim 1, wherein the module periodically checks an effectiveness of the diagnostic function.

5. The electronic module of claim 1, wherein the transferred function continuously controls an internal variable of the module.

6. The electronic module of claim 1, wherein the transferred function performs a function that is selected from the group comprising of determination of measured values on the basis of sensor measuring data, deduction of other measured values on the basis of already determined measured values, output of measured values and diagnosis.

7. The electronic module of claim 1, wherein the module is integrated into one of a level measuring device, a pressure measuring device and a density measuring device.

8. The electronic module of claim 1, wherein the module is integrated into one of a control device for a level measuring device, a pressure measuring device and a density measuring device.

9. The electronic module of claim 1, wherein the module is integrated into one of an evaluation and operating unit for a level measuring device, a pressure measuring device and a density measuring device.

10. The electronic module of claim 1, wherein the safety relevant data exchange occurs unidirectionally from the first area to the second area.

11. The electronic module of claim 1, wherein the first area is two-tier, one tier having a higher criticality than the other and the electronic module further comprises a component arranged in the higher criticality tier of the first-area, and wherein the component checks, during execution of the safety function, an effectiveness of the diagnostic function.

12. The electronic module of claim 1, wherein the safety function is performed from within the first area.

13. The electronic module of claim 1, wherein only the second area performs a transferred function of the module.

14. A device, comprising:
    an electronic module including a first area being categorized as safety-critical and a second area being categorized as safety-uncritical, the second area performing a transferred function of the module and the first area not performing the transferred function,
    wherein the module performs a safety function, the transferred function being categorized as a safety-critical and affects the safety function; and
    wherein the first area performs a diagnostic function in order to check an execution of the transferred function in the second area.

15. The device of claim 14, wherein the device is integrated into one of a field device, a control device and an evaluation and operating unit.

16. The device of claim 14, wherein the safety relevant data exchange occurs unidirectionally from the first area to the second area.

17. The device of claim 14, wherein only the second area performs a transferred function of the module.

18. A method for measuring and determining one of a level, a pressure and a density of a medium in a container using a field device, comprising:
    performing a safety function in a first area of an electronic module of the device that is categorized as safety-critical;
    performing a transferred function of the electronic module that is categorized as safety-critical and affects the safety function in a second area of the electronic module, the first area not performing the transferred function; and
    performing a diagnostic function in the first area in order to check an execution of the transferred function in the second area;
    wherein the second area is categorized as safety-uncritical.

19. The method of claim 18, further comprising:
taking a suitable measure if an error is detected in the transferred function; and periodically checking an effectiveness of the diagnostic function.

20. The method of claim 18, further comprising: unidirectionally exchanging safety relevant data from the first area to the second area.

* * * * *